(12) United States Patent
Marquess

(10) Patent No.: US 8,568,975 B2
(45) Date of Patent: Oct. 29, 2013

(54) SORTING SYSTEM FOR CATTLE

(76) Inventor: Leigh Marquess, Saskatoon (CA)

( * ) Notice: Subject to any disclaimer, the term of this patent is extended or adjusted under 35 U.S.C. 154(b) by 369 days.

(21) Appl. No.: 13/091,702

(22) Filed: Apr. 21, 2011

(65) Prior Publication Data
US 2011/0268835 A1 Nov. 3, 2011

Related U.S. Application Data

(63) Continuation-in-part of application No. 12/662,668, filed on Apr. 28, 2010, now abandoned.

(51) Int. Cl.
*C12Q 1/68* (2006.01)
*C07D 487/06* (2006.01)
*A01K 1/10* (2006.01)

(52) U.S. Cl.
USPC ....... 435/6.1; 514/214.02; 540/79; 119/51.01

(58) Field of Classification Search
None
See application file for complete search history.

(56) References Cited

U.S. PATENT DOCUMENTS

2003/0219819 A1 11/2003 Marquess

OTHER PUBLICATIONS

Engler et al. Impact of a Leptin SNP and Zilpaterol Hydrochloride on Growth and Carcass Characteristics of Finishing Steers. Abstract from the 2009 Beef Improvement Federation Annual Research Symposium and Annual Meeting, Apr. 30-May 3 in Sacramento CA. obtained from http://www.bifconference.com/bif2009/ab_c2_5_engler.html; two pages.*
Avendano-Reyes, L. et al., "Effects of two beta-adrenergic agonists on finishing performance, carcass characteristics, and meat quality of feedlot steers, "J. Anmic., Sci., vol. 84(12) (2006) pp. 3259-3265.
Buchanan, F.C. et al., "The leptin ARg25Cys affects performance, carcass traits and serum leptin concentrations in beef," Can. J. of Anim. Sci., vol. 87 (2007) pp. 153-156.
Dalrymple, R.H. et al., "A repartitioning agent to improve performance and carcass composition of broilers," J. Poult. Sci., vol. 63(12) (1984) pp. 2376-2383.
Eng, K.S. et al, "Latest zilpaterol studies reviewed," Feedstuffs, vol. 82(16) (Apr. 19, 2010) p. 12.
Geary, T.W. et al., "Leptin as a predictor of carcass composition in beef cattle," J. Anim. Sci., vol. 81 (2003) pp. 1-8.
Gruber, S.L. et al., "Effects of ractopamine supplementation on growth performance and carcass characteristics of feedlot steers differing in biological type," J. Anim. Sci., vol. 85 (2007) pp. 1809-1815.
Guiroy, P.J. et al., "The effects of implant strategy on finished bogy weight of beef cattle," J. Anim. Sci., vol. 80 (2002) pp. 1791-1800.
Houseknecht, K.L. et al., "The biology of leptin: a review," J. Anim. Sci., vol. 76(5) (1998) pp. 1405-1420.
Jéquier, E., "Leptin Signaling, Adiposity, and Energy Balance," Annals of the New York Academy of Sciences, vol. 967(1) (2002) pp. 379-388.
Johnson, B.J. et al, "Alterations in the physiology of growth of cattle with growth enhancing components," Veterinary Clinics Food Animal Practice, vol. 23(2) (2007) pp. 321-332.
Kim, K.S. et al., "A Missense variant of the porcine melanocortin-4 receptor (MC4R) gene is associated with fatness, growth, and feed intake traits," Mammalian Genome, vol. 11 (2000) pp. 131-135.
Kononoff, P.J. et al., "The effect of a leptin single nucleotide polymorphism on quality grade, yield grade, and carcass weight of beef cattle," J. Anim. Sci., vol. 83 (2005) pp. 927-932.
Marchant-Forde, J.N. et al., "The effects of ractopamine on behavior and physiology of finishing pigs," J. Anim. Sci., vol. 81 (2003) pp. 416-422.
Mersmann, H.J., "Overview of the effects of beta-adrenergic receptor agonists on animal growth including mechanisms of action," J. Anim. Sci., vol. 76 (1998) pp. 160-172.
Mils, S.E. "Biological basis for the ractopamine Response," Journal of Animal Science, vol. 80 (2002) pp. E28-E32.
Montgomery, J.L. et al., "Dietary Zilpaterol Hydrochloride. I Feedlot performance and carcass traits of steers and heifers," J. Anim. Sci., vol. 87 (2009) pp. 1374-1383.
Smith, S.B. et al., "Elevation of a specific mRNA in longissimus muscle of steers fed ractopamine," J Anim. Sci., vol. 67 (1989) pp. 3495-3502.
Spurlock, M.E. et al., "The effect of ractopamine on beta-adrenoceptor density and affinity in procine adipose and skeletal muscle tissue," J. Anim. Sci., vol. 72(1) (1994) pp. 75-80.
Vasconcelos, J.T. et al., "Effects of duration of zilpaterol hydrochloride feeding and days on the finishing diet on feedlot cattle performance and carcass traits," J. Anim. Sci., vol. 86(8) (2008) pp. 2005-2015.
Verhoeckx, K.C.M. et al., "Inhibitory effects of the $\beta_2$-adrenergic receptor agonist zilpaterol on the LPS-induced production of TNF-$\alpha$ in vitro and in vivo," J. Vet. Pharm. Therap., vol. 28(6) (2005) pp. 531-537.
Zhang, F. et al., "Crystal Structure of the *obese* protein leptin-E100," Nature, vol. 387 (6629) (May 8, 1997) pp. 206-209.

* cited by examiner

*Primary Examiner* — Juliet Switzer
(74) *Attorney, Agent, or Firm* — Frost Brown Todd LLC

(57) ABSTRACT

Disclosed herein is a method of sorting, treating, and feeding a group of bovine animals in a feed lot, wherein the method may include the steps of determining an ob genotype of each animal, comparing the relative weight and back fat of each animal with the other animals, dividing the animals into subgroups based on weight, back fat, and ob genotype. Zilpaterol hydrochloride (ZH) may be added to a feed ration fed to animals only in selected subgroups. Each group is fed a finishing period and then moved lot to slaughter. Each slaughter date and finishing period is independent of other subgroups.

10 Claims, 1 Drawing Sheet

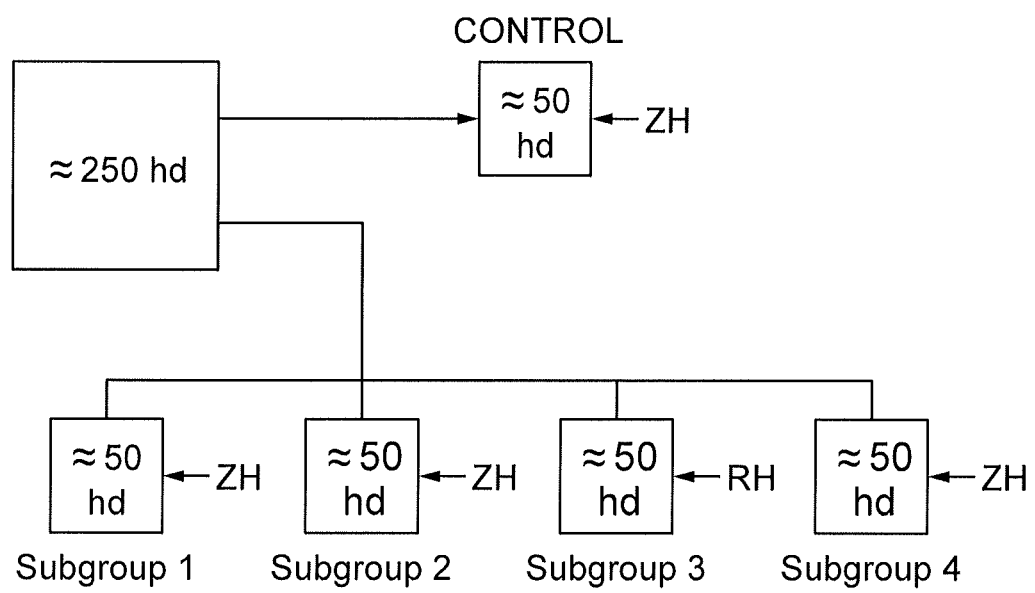

SORTING SYSTEM FOR CATTLE

This application is a continuation-in-part of and claims priority to U.S. application Ser. No. 12/662,668, filed Apr. 28, 2010, the disclosure of which is incorporated herein by reference.

The typical process of raising beef cattle starts with a rancher breeding cows and producing calves that feed on the mother's milk. The calves are weaned several months after birth and then fed on pastures, hay, or the like until they are essentially fully grown, at which time the animal enters a finishing feed lot. When the cattle are finished they are sold to a packer who slaughters and process the beef for sale to the public.

In the feed lot the object is to feed the animal the proper ration of feed so that it will most quickly obtain the proper market characteristics that are desired at that given time. When the cattle are finished they are sold to a packer who slaughters and processes the beef for sale to the public.

Once the cattle are sold from the feed lot to the packer they are slaughtered and the carcasses are hung on a rail where they can be graded according to national grading standards. Typically these standards are largely dependent on the amount of fat measured at certain defined and standardized points on the carcass. A selected one of these fat measurements is accepted as correlating to the amount of intramuscular fat in the carcass, and a quality grade is accorded to the carcass based on same. A carcass with a fat measurement at or above a certain standard measurement will be graded Prime in Canada and the United States. A carcass with a fat measurement less than that set for the Prime grade, but above the standard set for AAA grade in Canada, corresponding to Choice Grade in the United States, will grade AAA. A carcass with a fat measurement less than that set for AAA grade, but above the standard set for AA grade in Canada corresponding to Select grade in the USA, will grade AA, while those with fat measurements below the standard set for AA be graded correspondingly lower through the range of grades.

The most desirable grade in the present market is Prime, because fat is equated with palatability, lending juiciness and flavor to the meat, and is presently seeing demand from consumers. However since only a very small percentage of carcasses achieve this Prime grade, in practice producers aim to achieve the next most desirable grade which is AAA in Canada and Choice in the United States.

Significant premiums are presently being paid for carcasses grading AAA. In contrast, premiums have been historically been seen for leaner beef. At any given time then, the consumer will indicate his preference at the retail shelf, and this will send signals back through the chain to the packer, feeder, and cow/calf operators to aim for more or less fat.

Conventionally, the chain has reacted to these signals by switching breeds. Broadly speaking, European breeds such as Charolais and Limousin have bigger frames and leaner meat than British breeds such as Hereford and Angus. When lean beef is in demand, the feed lot will pay premiums for cattle bearing traits of European breeds, and when fat beef is in demand, premiums are paid for cattle bearing traits of British breeds.

Another major factor in the price realized by the feed lot operator is the yield grade, which is the percentage of usable meat that is derived from a carcass. Yield grade is dictated by a maximum subcutaneous fat measurement, but is a grade that is independent of the quality grade. While the minimum fat measurement for AAA quality grade may be achieved, exceeding that measurement can cause a reduction in yield grade, and therefore a reduction in price. For each yield grade there is a maximum fat measurement, such that exceeding the maximum fat measurement for Yield Grade 1 drops the carcass to a Yield Grade 2, and exceeding a maximum fat measurement for Yield Grade 2 drops the carcass to a Yield Grade 3, and so forth. Essentially the yield grade accounts for excessive fat on the carcass that must be trimmed prior to sale, and is therefore waste.

Thus, to realize the maximum price for a carcass in a market like that at present where the AAA quality grade is in demand, the feed lot operator must meet the minimum fat measurement for AAA quality grade, and yet not exceed the maximum fat measurement for Yield Grade 1. Present methods used to achieve this goal comprise visually grouping cattle according to frame type, estimated age and estimated weight at the time the cattle enter the feed lot. The animals of a particular group are fed and otherwise maintained substantially uniformly until it is estimated, again on the basis of experienced visual inspection, that the mean body condition of animals in the group is such that the measurement of fat will exceed the minimum required for AAA quality grade, yet be below the maximum allowed for Yield Grade 1.

In addition to quality and yield grades, other factors also influence the price received for a carcass. For example the weight of the carcass should fall in a desired range that provides the most popular size of cuts of meat.

Regardless of the particular market preference at any given time, the feed lot operator will be trying to tailor his cattle to meet some similar standard that will cause a meat packer or like commercial purchaser to pay the highest price in accordance with currently prevailing market preferences. Invariably some carcasses from the animals in a group fall in the desired range, while many are outside the desired range. Thus some of the carcasses will bring the maximum price because they are in the desired range, but a great many will bring a reduced price because they are outside the desired range. The price reduction generally increases in steps as variation from the desired range increases.

The feed lot operator's costs include the costs of operating the feed lot, such as labor, capital, maintenance, etc., plus the cost of feeding the cattle. While the cost of acquiring each animal in a group can vary somewhat, the feed lot operator's costs are the same for each animal in the group since they are fed the same amount of feed and occupy space in the feed lot for the same amount of time. Thus the price reductions for carcasses falling outside the desirable range fall directly to the feed lot operator's bottom line, reducing profits.

The feed lot operator has a very complex set of factors to consider when making decisions regarding feeding and marketing cattle. The longer the animal is in the feed lot before sale, the more it has cost the feed lot operator. At some times, keeping animals longer might be an attractive option if by doing so a more profitable grade can be achieved. For instance when body fat is in demand, the feed lot might keep the animals longer to fatten them more in order to have more cattle reach the AAA grade. This is especially true where yield grade deductions for excess fat are less than quality grade premiums for sufficient intramuscular fat, and even more so at times when sufficient animals are not available to bring into the feed lot, or when the price for same is high. Also, while it is desirable to move cattle out of the feed lot as early as possible to maximize throughput and reduce feed costs, there is considerable expense in buying, sorting, medicating, and like operations on each animal and so keeping a group of animals on feed for some extended period to achieve a better result can easily over ride the advantages of early slaughter.

Historically, cattle entering a feed lot were divided into groups according to phenotypical characteristics such as estimated age, frame size, breed, weight, sex and so forth. By doing this the feed lot owner is attempting to group the cattle so that the group can be penned together, receive the same feed ration and hormone or drug treatments, and will be ready for market at the same time. Weight and visual clues were the only means available to sort cattle for feed lot grouping. More recently genetic classifications have been developed and used to sort cattle into groups with the same genotype.

For example in United States Published Patent Application Number 2003/0219819 to Marquess, the disclosure of which is incorporated herein in its entirety by reference, the homozygosity or heterozygosity of each animal with respect to alleles of a gene encoding an adipocyte-specific polypeptide, termed leptin, which gene is hereinafter referred to as "ob" is determined when the cattle are received at the feed lot. The ob genotype, in particular homozygosity in respect of a first ob allele, homozygosity in respect of a second ob allele, or heterozygosity in respect of the first and second ob alleles, is determined. It has been found that cattle that are homozygous for the T single nucleotide polymorphism ("SNP") (hereinafter "TT cattle") are the most genetically predisposed to lay down fat. Cattle that are homozygous for the C SNP (hereinafter "CC cattle") are the least genetically predisposed to lay down fat, and cattle that are heterozygous for the SNP (hereinafter CT cattle) are in between, i.e. less genetically predisposed to lay down fat than TT cattle and more predisposed to lay down fat than CC cattle.

The cattle are then sorted into groups with TT in one group, CT cattle in another group, and CC cattle in still another group. These groups based on genotype may be further subdivided by phenotypical characteristics such as frame size, weight, color, and the like. The animals in each final group are then penned together and receive the same ration and hormones or drugs, and are sold for slaughter at the same time.

The feed ration fed to cattle in a feed lot is generally the same for all cattle and is designed to provide the maximum amount of energy that the animal can process without suffering from bloat or like digestive problems, and so provide the maximum possible weight gain on the animal. The main difference once the cattle are sorted is the number of days each group is kept before slaughter. For example the CC cattle that are least genetically predisposed to lay down fat may be fed a shorter time with the aim to achieve a lower fat grade, or a lean grade, rather than feed them longer to achieve the high fat grade, since fewer of the CC cattle will likely achieve the required fat level even if kept longer. Alternatively, when the market price of the quality grades proves sufficient to cover the increased cost of feeding the CC animals longer to obtain a higher percentage of CC animals reaching the AAA quality grade, these animals may be fed longer than the TT animals in order to reach the desirable quality grade status.

The TT cattle that are most genetically predisposed to lay down fat may be fed longer to achieve a high fat grade. Alternatively, TT animals may be fed the shortest duration in comparison to the CT & CC animals since they will reach any given amount of target fat earlier than the rest of the animals. The CT cattle that are intermediately genetically predisposed to lay down fat can be fed longer to achieve a high fat grade, or shorter to achieve a lean grade, depending on considerations such as market prices, price trends, feed costs, availability of further feeder cattle to bring into the feed lot, and other like external considerations. On occasion such external considerations may also dictate that CC cattle should be fed for a fat grade.

A practical problem arises in that the animals are typically passed through a chute and sorted into groups when they enter the feed lot, and since it takes some time to determine the genotype, it is necessary to then bring the cattle back to the chute and re-sort them after genotypes have been determined.

As described in United States Published Patent Application Number 2010/0305101 to Marquess, the disclosure of which is incorporated in its entirety herein by reference, a class of compounds known as beta-adrenergic agonists (hereinafter, "beta-AA") has more recently been used in the livestock industry as feed additives to improve feed conversion efficiency and increase the amount of weight gained by cattle in a feedlot. Two beta-AAs that are commercially available to beef producers are zilpaterol hydrochloride ("ZH"), marketed by Merck & Co of New Jersey, USA as Zilmax®, and ractopamine hydrochloride ("RH"), marketed by Elanco of Indiana, USA as Optaflexx®.

Either ZH or RH (not both) is added to the feed ration fed to pens of animals contained in a feedlot, starting at some defined period just prior to slaughter. For example, Optaflexx® (RH) is registered in Canada and the USA for feeding during the 28-42 days prior to slaughter, with no withdrawal time required. Zilmax® (ZH) is registered for feeding during the 20-40 days prior to slaughter with a three day withdrawal period before slaughter. Feeding either ZH or RH for periods beyond the registered label time frames is not permitted by law, and biologically extended feeding also has diminishing economic returns and eventually will have no advantage over animals which have never had any beta-adrenergic agonists administered to them at all These beta-adrenergic agonists promote the deposition of lean muscle tissue at the expense of fat tissue by shifting nutrient use toward carcass lean tissue deposition and away from fat tissue. Comparisons to non-treated steers showed a hot carcass weight ("HCW") increase of 14 kgs (30.8 lbs) for RH and 22 kgs (48.5 lbs) for ZH. Both RH and ZH have also been found to increase toughness of the muscle tissue (Avendano-Reyes, L., Torres-Rodriguez, V., Meraz-Murillo, F. J., Perez-Linares, C., Figuearoa-Saavedra, F. and P. H. Robinson, Effects of two beta-adrenergic agonists on finishing performance, carcass characteristics, and meat quality of feedlot steers. *J. Anim. Sci.* 84(12):3259-65 (2006)). Thus beta-adrenergic agonists have both beneficial and detrimental effects on those features that relate to the price paid for a beef carcass.

Zilmax® (ZH) administered to cattle has been shown to increase hot carcass weight, final body weight and yield grade, but it also reduces subcutaneous fat, marbling score, and thus the quality grade. Ribeye area ("REA") is also increased, which is somewhat detrimental in that it is desirable to have REA within a desired range so that retail cuts are uniform. Excessive REA can result in discounts at the packer. Zilmax® is also recognized to reduce the tenderness of meat as determined using the Warner-Bratzler shear analysis. While Zilmax® (ZH) purportedly converts feed eaten more efficiently so that more weight is gained, in United States Published Patent Application Number 2010/0305101 it is demonstrated that Zilmax® (ZH) application does reduce feed intake to certain genotypes (TT & CT animals). Therefore it is likely that the conversion of feed to meat is different amongst the three genotypes.

Similarly Optaflexx® (RH) administered to cattle has been shown to improve average daily gain ("ADG"), gain to feed, feed conversion ("G:F"), and hot carcass weight ("HCW") while having a reduced detrimental effect on subcutaneous fat, marbling score, and thus the quality grade compared to ZH application.

In 2010/0305101, Marquess describes a system where, in one embodiment, animals are sorted according to ob genotype and where ZH is administered to only CC animals in order to avoid the adverse effect of reduced marbling in the CT and TT animals, and to optimize hot carcass weight gain (the largest in CC animals), optimize rib eye area gain (the smallest in CC animals), and not suffer the adverse effects of reduced dry matter intake during ZH administration in the CT and TT animals. In another embodiment the system may comprise CC animals receiving ZH administration along with a lighter weight subgroup of the CT animals which would optimize hot carcass weight gain response along with marbling response in those animals which are most probable candidates for ZH treatment so as to avoid excessive HCW gain which would result in final HCW which is above a weight which results in a discount from the packer for excessive weight.

In still another embodiment the system may comprise TT animals not receiving any ZH treatment and receiving either no beta-adrenergic agonist treatment or alternatively RH treatment in order to optimize the marbling response of animals and avoid any adverse consequences of ZH treatment, and potentially receive the weight gain benefits from RH treatment. In still another embodiment the system may comprise feeding all animals ZH except black hided TT's and/or black hided CT's in order to allow animals to express their maximum genetic potential for marbling, which will increase the probability of reaching the Certified Angus Beef® Quality standards, which represent a considerable premium. This same system would have the black hided TT and/or CT animals receive either RH treatment or no beta-adrenergic agonist treatment.

Thus, the beneficial aspects of beta-adrenergic agonists are available for those cattle that will most benefit therefrom, while the detrimental effects are prevented in those cattle where the detrimental effects are most likely to outweigh the beneficial effects.

Specifically, application of Zilmax® to CC genotype animals yields results that are larger than "label" or expected response in HCW, and small or no reduction in marbling and quality grade (USDA Choice or better). In addition, REA size is optimal when it is kept to a size such that an acceptable portion size can be obtained, which in practice means that as the REA continues to get larger, beyond a threshold, it is detrimental. Therefore, as Zilmax® is known to increase REA size, feeding Zilmax® to CC's can limit the downside in this area, as the increase in rib eye area ("REA") is significantly less in CC animals than in TT or CT animals.

Conversely, when observing the TT animals fed Zilmax® it is clear that there are specific detrimental effects on important features. Marbling is significantly reduced in TT animals fed Zilmax®, especially in comparison to CC animals, which is a contributor to the reduction in quality grade. Also, TT animals fed Zilmax® have the largest increase in REA size, which is detrimental to portion size acceptance. Also, importantly, these same TT animals have a smaller than expected or label HCW gain when compared to CC & CT animals. Again these same TT animals fed Zilmax® have a reduced dry matter intake ("DMI") during the feeding phase when compared to TT animals not fed Zilmax®, thus reducing the potential for profitable gain above an animal's maintenance costs. This clearly has a negative impact on the value of feeding Zilmax®.

Thus the "label" or expected weight gains tested and accepted as accruing to the use of Zilmax® are not evenly distributed among cattle with different ob genotypes. The testing is based on cattle groups including an undifferentiated blend of CC, CT, and TT animals, and a "label" gain calculated as the gain of the group divided by the numbers in the group. The present testing indicates that in fact there are considerable differences in weight gains between CC, CT, and TT animals, and management of the animals based on ob genotype can lead to more effective use of beta-adrenergic agonists such as Zilmax®, with increased advantage taken from the beneficial aspects of the compounds, and reduced disadvantages resulting from the detrimental aspects of the compounds.

SUMMARY OF THE INVENTION

This invention is in the field of agricultural animal management and in particular a method of sorting cattle in a feed lot to increase profit.

It is an object of the present invention to provide a method of sorting cattle in a feed lot that overcomes one or more problems in the prior art.

The present invention provides a method of sorting, treating, and feeding a group of bovine animals in a feed lot. The method may comprise determining a weight of each animal, and comparing the weight of each animal with the weight of the other animals in the group; determining an ob genotype of each animal, the ob genotype determined by whether the animal is a TT animal homozygous with respect to the T-allele of the ob gene, a CC animal homozygous with respect to the C-allele of the ob gene, or a CT animal heterozygous with respect to the T-allele and the C-allele of the ob gene; determining a back fat measurement of each animal, and comparing the back fat measurement of each animal with the back fat measurement of the other animals in the group; dividing the animals into a plurality of subgroups wherein: a first subgroup includes at least CC animals with comparatively less weight and back fat, a final subgroup includes at least CT and TT animals with comparatively more weight and back fat, at least one intermediate subgroup includes animals with intermediate weight and back fat; at a selected date prior to a slaughter date, adding zilpaterol hydrochloride (ZH) to a feed ration fed to animals only in selected subgroups, such that animals in unselected subgroups receive no ZH; and feeding each subgroup for a finishing period subsequent to the selected date and then moving the animals from the feed lot to slaughter. All CC animals are in selected subgroups receiving ZH, and only CT animals and TT animals are present in unselected subgroups receiving no ZH. CC animals, CT animals and TT animals are present in all selected subgroup receiving ZH. The slaughter date and finishing period for each subgroup is independent of the slaughter date and finishing period for other subgroups.

The sorting system of the present invention provides increased returns due to increased carcass weight as well as improved quality and yield grades which result in an increased price per pound.

DESCRIPTION OF THE DRAWINGS

While the invention is claimed in the concluding portions hereof, preferred embodiments are provided in the accompanying detailed description which may be best understood in conjunction with the accompanying diagrams where like parts in each of the several diagrams are labeled with like numbers, and where:

FIG. 1 is a schematic depiction of the study.

DETAILED DESCRIPTION

The present invention provides a method of sorting, treating, and feeding a group of bovine animals in a feed lot. In one embodiment the method may comprise determining a weight of each animal, and comparing the weight of each animal with a weight of the other animals; determining whether each animal is a TT animal homozygous with respect to the T-allele of the ob gene, a CC animal homozygous with respect to the C-allele of the ob gene, or a CT animal heterozygous with respect to the T-allele and the C-allele of the ob gene; and determining a back fat measurement of each animal, and comparing the back fat measurement of each animal with a back fat measurement of the other animals.

The animals are then divided into subgroups where a first subgroup includes at least CC animals with comparatively less weight and back fat; a final subgroup includes at least TT animals with comparatively more weight and back fat; at least one intermediate subgroup includes animals with intermediate weight and back fat. Typically, there are two intermediate subgroups including animals with intermediate weight and back fat.

All CC animals are in selected subgroups receiving ZH, and only CT animals and TT animals are present in unselected subgroups receiving no ZH. The detrimental effects of ZH on CC animals are relatively small compared to the effects on CT and TT animals, and so the beneficial effects of ZH outweigh the detrimental effects for all the CC animals. CC animals, CT animals and TT animals are present in all selected subgroup receiving ZH.

After sorting, at a selected date prior to slaughter, a recommended amount of zilpaterol hydrochloride (ZH) is added to the feed ration of animals in selected ones of the subgroups, and animals in unselected subgroups receive no ZH. Each subgroup is then fed for a finishing period subsequent to the selected date and then the animals are moved from the feed lot to slaughter.

Each subgroup is observed and the slaughter date for each is determined independently of the other subgroups using conventional measures, predominantly a visual judgment of the readiness of cattle in the group. The finishing period for each subgroup is independent of the finishing period for other subgroups, and will generally be different than for any other subgroup, except on exceptional coincidental occasions.

The method of the invention thus subgroups the cattle in any group according to genotype, and relative weight and back fat. In a typical application of the method, cattle are brought into a feed lot and fed the conventional ration for an initial period until the date when ZH treatment is typically done. The commercially available form of ZH, Zilmax®, is registered in Canada and the USA for feeding during the 20-40 days prior to slaughter with a three day withdrawal period. The subgrouping of the present method occurs just prior to the addition of ZH to the feed ration.

TABLE 1

| wt-gt-color-bf | Subgroup |
|---|---|
| 1CCNB0 | 1 |
| 1CCNB1 | 1 |
| 1CCB0 | 1 |
| 1CCB1 | 1 |
| 1CTNB0 | 1 |
| 1CTNB1 | 1 |
| 1CTB0 | 1 |
| 1CTB1 | 1 |
| 1TTNB0 | 1 |
| 1TTNB1 | 1 |
| 1TTB0 | 1 |
| 1TTB1 | 1 |
| 2CCNB1 | 1 |

TABLE 1-continued

| | |
|---|---|
| 2CCB1 | 1 |
| 2CTNB1 | 1 |
| 2CTB1 | 1 |
| 1CCNB2 | 2 |
| 1CCB2 | 2 |
| 1CTNB2 | 2 |
| 1CTB2 | 2 |
| 1TTNB2 | 2 |
| 1TTB2 | 2 |
| 2CCNB0 | 2 |
| 2CCNB2 | 2 |
| 2CCB0 | 2 |
| 2CCB2 | 2 |
| 2CTNB0 | 2 |
| 2CTNB2 | 2 |
| 2CTB0 | 2 |
| 2CTB2 | 2 |
| 3CCNB0 | 2 |
| 3CCNB1 | 2 |
| 3CCNB2 | 2 |
| 3CCB0 | 2 |
| 3CCB1 | 2 |
| 3CCB2 | 2 |
| 3CTNB2 | 2 |
| 3CTB2 | 2 |
| 2TTNB0 | 3 |
| 2TTNB1 | 3 |
| 2TTB0 | 3 |
| 2TTB1 | 3 |
| 2TTB2 | 3 |
| 3CTNB0 | 3 |
| 3CTNB1 | 3 |
| 3CTB0 | 3 |
| 3CTB1 | 3 |
| 3TTNB0 | 3 |
| 3TTNB1 | 3 |
| 3TTB0 | 3 |
| 3TTB1 | 3 |
| 3TTB2 | 3 |
| *3TTNB2 | 3 |
| *2TTNB2 | 3 |
| 4CCNB0 | 4 |
| 4CCNB1 | 4 |
| 4CCNB2 | 4 |
| 4CCB0 | 4 |
| 4CCB1 | 4 |
| 4CCB2 | 4 |
| 4CTNB0 | 4 |
| 4CTNB1 | 4 |
| 4CTNB2 | 4 |
| 4CTB0 | 4 |
| 4CTB1 | 4 |
| 4CTB2 | 4 |
| 4TTNB0 | 4 |
| 4TTNB1 | 4 |
| 4TTNB2 | 4 |
| 4TTB0 | 4 |
| 4TTB1 | 4 |
| 4TTB2 | 4 |

*previously in Group 2

| Weight | GT | Color | BF |
|---|---|---|---|
| 1 = lightest | CC | NB = not black | 1 = leanest |
| 4 = heaviest | CT | B = black | 2 = fattest |
| | TT | | |

An example of a sorting guide is illustrated in Table 1. Table 1 illustrates a grouping where the cattle are also divided by color. The color of each animal is determined and compared with a desired color, and each animal is assigned to a subgroups further based on the color of each animal. In Table 1, the desired color is black, and each animal is categorized as either "black" (B) or "not black" (NB). This is a recognition of the success of a branding program for Certified Angus Beef® which has resulted in fat black cattle, which attain certain quality standards, presently receiving a price premium over fat cattle of the same quality that are any other color, i.e.

not black. Similar premiums and/or discounts for other characteristics can be incorporated in the present method if warranted.

In the example, the step of determining the weight of each animal, and comparing the weight of each animal with a weight of the other animals is practiced by dividing the animals into a number of weight divisions with a first division including the relatively lightest animals progressing through to a final division including the relatively heaviest animals. In the example the number of weight divisions is equal to the number of subgroups, e.g., four. The allocation of an animal to a weight division is determined by determining the weight of each animal, ordering all the animals in sequential order according to weight, dividing the number of animals by the number of subgroups to determine the number of animals in each weight division, and sequentially allocating each animal to a weight division.

Thus, all the cattle in the group are weighed and identified as belonging in a weight division by assigning a number to each according to its relative weight. For example, those animals with a weight in the lightest 25% or quartile of the group are assigned to weight division "1," animals with a weight in the next heaviest 25% are assigned to weight division "2," the animals with a weight in the next heaviest 25% are assigned to weight division "3," and finally animals with a weight in the heaviest 25% are assigned to weight division "4."

In the example, the step of determining whether each animal is a TT animal homozygous with respect to the T-allele of the ob gene, a CC animal homozygous with respect to the C-allele of the ob gene, or a CT animal heterozygous with respect to the T-allele and the C-allele of the ob gene is carried out at any point prior to the time when the subgroups are made. Typically a tissue sample is taken when the animal is first brought into the feed lot and the ob genotype is determined in a lab from the sample, such that when the subgrouping takes place at a later date, the genotype for each animal is known.

In the example, the step of determining a back fat measurement of each animal, and comparing the back fat measurement of each animal with a back fat measurement of the other animals is practiced by measuring the back fat of all the animals in the group, such as by ultrasound, and assigning each animal a back fat factor according to its relative back fat. In the example, three back fat factors are used: "1" indicates the leanest animals, those which have a back fat measurement which is two or more standard deviations below the mean of all back fat measurements, "0" indicates the averagely fat animals, those which have back fat measurements which fall within two standard deviations above or below the mean of all back fat measurements, and "2" indicates the fattest animals, those which have a back fat measurement which is two or more standard deviations above the mean of all back fat measurements. The selection of the measure of the standard deviation from the mean value of the group may change as market conditions dictate, that is the exact definition for "1" and "2". In the example above where the deviation from the mean for the leanest and fattest subgroups is two standard deviations, about 95% of cattle will fall in the averagely fat group "0," while about 2.5% will be in the leanest group "1" and about 2.5% will be in the fattest group "2". If the measure was changed from 2.0 standard deviations to 1.0 standard deviations about 68% of cattle will fall in the averagely fat group "0", while about 16% will be in the leanest group "1" and about 16% will be in the fattest group "2".

While the cattle at these extremes of fat and lean are few in number, the proper management and feeding of the cattle at these extremes generally results in significantly improved returns from each animal that justify separating the small numbers. The returns for these cattle on the extremes of fat and lean are generally significantly larger than the returns from the method for more average cattle in the middle of the fat spectrum.

It is contemplated that instead of dividing the cattle at 2.0 standard deviations above and below the mean it may be advantageous to include more cattle in the fattest and leanest divisions by dividing at 1.5 or 1.75 or some other number of standard deviations above and below the mean that is less than 2.0.

Thus in the example of Table 1, each animal will be:
1. in one of the weight quartiles indicated by 1, 2, 3, or 4
2. CC, CT, or TT ob genotype
3. black B or not black NB
4. in one of the 3 back fat values indicated by 1, 0, or 2.

Thus there are a total of 4 (weight)×3 (ob genotype)×2 (color)×3 (back fat)=72 possible combinations of subgrouping factors, and each animal will have one of these combinations. While it is theoretically possible to subgroup the original group into 72 subgroups, such a large number is not practical, and in any event it is contemplated that such a fine division is not warranted by the benefits that would be obtained. In the example therefore it was decided that four subgroups 1, 2, 3, and 4 would be used, and animals with each combination of subgrouping factors is assigned to one of the subgroups.

The object of the subgrouping is essentially to create some subgroups with animals which will realize a net benefit from treatment with ZH, and other subgroups with animals which will realize a net benefit by omitting treatment with ZH. An analysis is made of the known effects of ZH on the animals, notably increased hot carcass weight, final body weight, yield grade, and ribeye area ("REA") along with reduced tenderness, subcutaneous fat, marbling score, and quality grade, and the differing effects of ZH depending on ob genotype, and each combination is assigned to a subgroup based on that analysis.

In the present method the animals are divided into a number of weight divisions with a first division including the relatively lightest animals progressing through to a final division including the relatively heaviest animals. Since weight is a significant driver of the present method, the animals were sorted into four weight divisions from the lightest quartile designated as "1" and the heaviest quartile as "4", thus the same number of weight divisions as the selected number of subgroups.

As seen from Table 1, Subgroup 1 includes a first combination "1CCNB0" which indicates an animal that is in the lightest 25% of the cattle (1), is homozygous with respect to the C-allele of the ob gene (CC), is not black (NB), and is in the leanest group of the cattle. Going down the column it can be seen that Subgroup 1 includes:
1. the leaner CC, CT, and TT cattle in the lightest weight division (1), that have a back fat in the leanest and average fat groups of the cattle (BF=1 or 0), whether black or not; and
2. the leanest CC and CT cattle in the heavier weight division (2), that have a back fat in the leanest group of the cattle (BF=1), whether black or not.

Thus the first Subgroup 1 includes those CC animals with comparatively less weight and back fat compared to the rest of the animals in the original group.

Subgroup 2 includes only the fattest CC animals (BF=2) in the lightest weight division (1), and heavier CC animals. Subgroup 2 further includes:

1. the fattest CC animals in the lightest weight division (1) that have a back fat in the fattest group of animals (2), whether black or not;

2. the fat CT and TT animals in the lightest weight division (1) that have a back fat in the average fat and fattest groups of animals (0 or 2), whether black or not;

3. the fat CC and CT animals in the heavier weight division (2) that have a back fat in the average fat and fattest groups of animals (0 or 2), whether black or not;

4. all CC animals in the still heavier weight division (3) regardless of back fat and color;

5. the fattest CT animals (BF=2) in the still heavier weight division (3) whether black or not.

Subgroup 3 includes all TT animals in the intermediate weight divisions (2 or 3), and the leaner heavier CT animals in the heavier weight division (3). Subgroup 3 includes:

1. all TT animals in the intermediate weight divisions (2 or 3);

2. the leaner CT animals in the heavier weight division (3) that have a back fat in the leanest and average fat groups of animals (1 or 0), whether black or not;

3. no CC animals are in this subgroup.

It will be noticed that in Subgroup 3 the combinations 3TTNB2 and 2TTNB2 are at the bottom of the column, rather than in order higher up the column. This is because these two combinations were originally placed in Subgroup 2, and later moved to Subgroup 3 after further consideration—this movement is noted to indicate that allotting a combination to one subgroup or another is not a concrete determination, but involves a balancing of the influence of ZH on each characteristics, and the sometimes conflicting nature of these effects.

A final Subgroup 4 includes at least TT animals with comparatively more weight. In the example of Table 1, the final Subgroup 4 includes all CC, CT, and TT animals in the heaviest weight division (4) regardless of back fat and color.

In the example then of Table 1, animals in Subgroups 1, 2, and 4 will be administered a treatment of ZH, while animals in Subgroup 3 will receive no ZH.

The animals in Subgroup 1 are the lighter weight, leaner animals of all ob genotypes. In order for these animals to achieve a high enough marbling score to achieve high quality grades they need to be grouped and segregated together so as to ensure any potential for achieving a high quality grade is met, so while the reduced fat from treating with ZH will only be detrimental to the CT & TT animals, and they will be few in head count in relation to the rest of Subgroup 1, since they are light weight the added weight from a treatment of ZH will increase the carcass weight.

The animals in Subgroup 2 are fat but light animals of all ob genotypes, all the remainder of the CC animals that are in weight divisions 1, 2, and 3, and fatter and heavier CT animals. The reduced fat resulting from treatment with ZH is quite pronounced in TT and CT animals, but has a relatively smaller fat reduction effect on CC animals, so all CC animals are treated with ZH. The fatter CT and TT animals may still make an increased quality grade (fat) but these are the lighter fat CT and TT animals that will benefit from weight gain of ZH. These animals may be fed a decreased time relative to Subgroup 1, but longer than Subgroups 3 and 4.

The animals in Subgroup 3 are all TT animals in the intermediate weight divisions 2 and 3, and the leaner CT animals in the heavier weight division 3 that have a back fat in the leanest and average fat groups (1 or 0). These animals receive no ZH, as it is desired to add fat and/or maintain the existing high fat levels in order to achieve higher quality grades. These animals may be fed an increased time relative to all other subgroups to add fat to the greatest extent practical, or may be fed longer than Subgroups 1 & 2, but a shorter time frame than Subgroup 4.

Finally the animals in Subgroup 4 are all animals in the heaviest weight division 4, regardless of ob genotype, back fat, and color. These animals may receive ZH, depending on the market conditions of the day, and the weight of the animals on the sorting date once the sort is complete. That is, if enough weight is present in Group 4 animals, such that it is projected they will become heavy to a point where discounts are applied once the 21 day feeding of ZH is complete; then it may be decided to feed no ZH.

The animals in Subgroup 3 which receive no ZH may receive either no beta-AA treatment at all, or may receive RH in the feed ration instead, such as Optaflexx® (RH) which is registered in Canada and the USA for feeding during the 28-42 days prior to slaughter, with no withdrawal time required. Optaflex® has reduced detrimental effects on subcutaneous fat, marbling score, and thus the quality grade compared to ZH application, and may be beneficial in many cases.

In an embodiment of the method of the present invention in an actual feedlot, cattle arriving at the feedlot will be passed through a chute where, as in any conventional feed lot they are weighed, marked for identification, medicated, etc. While passing through the chute a tissue sample is taken from each animal and identified with the animal. The animals are sorted into pens conventionally by weight, color, etc. and then fed conventionally for several weeks until some time just before the conventional time of beginning to add ZH to the feed ration.

The ob genotype of the tissue samples is determined, typically by sending them to a remote lab since the results are not needed until sorting before the ZH is fed, and since such labs can often provide the reduced costs of a large scale testing operation. The ob genotype of each animal is thus known when the animals are passed through the chute just prior to the start of adding ZH to the feed ration (or not adding ZH as the case may be in the method of the present invention).

As the animals move through the chute they are weighed, back fat is measured (typically by ultrasound), and the color of the animal is noted, and this data is entered into a computer processor for each animal, along with the predetermined ob genotype for the animal. In order for the grouping system to work effectively the animals passing through the chute must be directed into a group before all the cattle have been weighed and measured, and in fact after only a very few cattle have been through the weighing and measuring process.

For the first animals a projected determination of the weight quartile into which they should fall will be based on an experienced estimate of the where the weight will fall. Similarly the grouping based on fat (1, 0, or 2) will be estimated based on the back fat measurement. As the animals are measured, the database of actual weights and back fat builds up and the subgroup placements become more accurate. The weight quartile divisions and mean back fat will vary somewhat as more animals pass through the chute and the data accumulates, but only cattle with weights and back fat on the boundaries may be in a subgroup that is not accurate when the final animal is through the chute and the relative back fat and weight divisions are finally determined.

A very long chute, or a plurality of chutes, could be provided that would allow the required data on a large number of animals to be accumulated before the first animal out of the chute was directed into one of the subgroups, but in most situations it is contemplated that this will not be practical, or even necessary for a beneficial use of the method of the present invention. It is contemplated that inaccuracies in subgroup placement of some of the cattle passing earlier through the chute will not unduly affect the operation. For example in one subgrouping operation on a group of cattle, after all animals had been through the chute it was determined that about 92% of the cattle were placed in the correct subgroups.

Once the sorting is complete the animals are penned in subgroups. An estimated slaughter date for each pen is determined, typically by conventional visual determination, and then ZH is added to the feed ration of Subgroups 1, 2, and 4 at a date backed off from the slaughter date as in conventional management procedures. The animals of Subgroup 3 receive no ZH but may receive RH in the feed ration instead, such as Optaflexx®, or may receive no beta-AA treatment at all. The animals in Subgroup 3, because of a combination of factors of ob genotype, weight, and fat along with projected yield and quality grades, are those wherein the detrimental effects of ZH outweigh the beneficial effects of ZH, while a like combination of factors dictates that with the animals in Subgroups 1, 2, and 4 the beneficial effects of ZH outweigh the detrimental effects of ZH.

In a study conducted at a private research facility in Texas, USA (Cactus Research, Amarillo Tex.) a total of 2696 steers (mostly yearling types at placement) were used in 10 replicates (blocks) in a randomized complete block design.

As schematically depicted in FIG. 1, each block (typically about 250 animals) was randomly sub-sampled to obtain approximately 50 unsorted control steers with the remaining steers sorted into 4 subgroups based on individual animal profiles of ob genotype, comparative weight and back fat, and color (black or not black). The sorting took place at approximately 45 days from what would have been the slaughter date of the unsorted lot.

The unsorted control animals were typically fed for 45 days after sorting before being slaughtered. An estimated slaughter date for each subgroup was then determined, which ranged from 25-90 days. Slaughter dates for all treatments were determined by a scheduler using typical procedures, primarily visual appraisal combined with visual appraisal of slaughter plant data feedback. In one block, for example, the days on feed before slaughter were as follows:

| | |
|---|---|
| Control group | 45 days |
| Subgroup 1 | 78 days |
| Subgroup 2 | 51 days |
| Subgroup 3 | 43 days |
| Subgroup 4 | 27 days |

As described above, in each block one of the four sorted subgroups (approximately 25% of the sorted cattle) was designated to be fed RH in the commercial form of Optaflexx®, but no ZH. The remaining sorted subgroups and all of the control groups were fed ZH in the commercial form of Zilmax®.

For the control group and each subgroup receiving ZH, the ZH was fed for 21 days followed by a 3-4 day withdrawal, and timed with respect to the estimated slaughter date of each subgroup such that after this withdrawal the animals went to slaughter.

Across the study, the sorted cattle were fed a total five additional days resulting from the scheduler moving some sorted groups up 14-28 days earlier than their respective controls and by the scheduler adding 21-49 days to other sorted groups beyond their respective controls.

On average, sorted cattle consumed a total of $7.27 per head more feed as a result of the extended feeding period averaging 5 days per animal (P=0.03) but returned $20.34 more revenue (P=0.002) than the unsorted control animals. Revenues increased through a combination of increased price resulting from better quality and yield grades and increased saleable carcass weight, which averaged 8 pounds of hot carcass weight. Price and weight each contributed approximately equally to increased revenue.

Interestingly the sorted animals averaged an increase of 8 pounds of hot carcass weight compared to the control animals even though 100% of the unsorted control animals were fed ZH, while only 75% of the sorted animals were fed ZH and 25% fed RH.

The data from the study indicate that the sorting system evaluated in this study can return a gross margin of approximately $13 per head ($20 revenue increase minus $7 added feed cost) above unsorted controls.

The foregoing is considered as illustrative only of the principles of the invention. Further, since numerous changes and modifications will readily occur to those skilled in the art, it is not desired to limit the invention to the exact construction and operation shown and described, and accordingly, all such suitable changes or modifications in structure or operation which may be resorted to are intended to fall within the scope of the claimed invention.

I claim:

1. A method of sorting, treating, and feeding a group of bovine animals in a feed lot, the method comprising the steps of:
   a.) determining a weight of each animal, and comparing the weight of each animal with the weight of the other animals in the group;
   b.) determining an ob genotype of each animal, the ob genotype determined by whether the animal is a TT animal, homozygous with respect to the T-allele of the ob gene, a CC animal, homozygous with respect to the C-allele of the ob gene, or a CT animal, heterozygous with respect to the T-allele and the C-allele of the ob gene;
   c.) determining a back fat measurement of each animal, and comparing the back fat measurement of each animal with the back fat measurement of the other animals in the group;
   d.) dividing the animals into a plurality of subgroups wherein:
      i.) a first subgroup includes at least CC animals with comparatively less weight and back fat;
      ii.) a final subgroup includes at least CT and TT animals with comparatively more weight and back fat; and
      iii.) at least one intermediate subgroup includes animals with intermediate weight and back fat;
   e.) adding zilpaterol hydrochloride at a selected date prior to a slaughter date to a feed ration fed to animals only in selected subgroups, such that animals in unselected subgroups receive no zilpaterol hydrochloride; and
   f.) feeding each subgroup for a finishing period subsequent to the selected date and then moving the animals from the feed lot to slaughter;
   wherein all CC animals are in selected subgroups receiving zilpaterol hydrochloride, and only CT animals and TT animals are present in unselected subgroups receiving no zilpaterol hydrochloride;
   wherein CC animals, CT animals and TT animals are present in all selected subgroup receiving zilpaterol hydrochloride; and wherein the slaughter date and finishing period for each subgroup is independent of the slaughter date and finishing period for other subgroups.

2. The method of claim 1 comprising administering a treatment of ractopamine hydrochloride to animals in unselected subgroups.

3. The method of any one of claims 1 and 2 comprising determining a color of each animal, and comparing the color of each animal with a desired color, and assigning animals to subgroups based on the color of each animal.

4. The method of claim 3 wherein the desired color is black, and wherein each animal is categorized as either "black" or "not black".

5. The method of claim 1 wherein the animals are divided into a number of weight divisions with a first division including lightest animals that are relatively lightest progressing through to a final division, wherein the final division includes animals that are relatively heaviest, and wherein the number of weight divisions is equal to the number of subgroups.

6. The method of claim 5 wherein the allocation of an animal to a weight division is determined by determining the weight of each animal, ordering all the animals in sequential order according to weight, dividing the number of animals by the number of subgroups to determine the number of animals in each weight division, and sequentially allocating each animal to the weight division.

7. The method of claim 1 wherein a tissue sample is taken from each animal when the animal enters the feed lot, and wherein the tissue sample is tested to determine the ob genotype of each animal.

8. The method of claim 7 wherein the tissue sample is sent to a remote facility for testing.

9. The method of claim 1 wherein each animal is assigned a back fat factor, and wherein the assignment of a back fat factor to an animal is determined by determining the back fat of each animal, determining the mean back fat of all the animals, assigning a first lean back fat factor to animals with a back fat measurement that is more than a selected number of standard deviations below the mean, assigning a second average back fat factor to animals with a back fat measurement within the selected number of standard deviations above and below the mean, and assigning a third fat back fat factor to animals with a back fat measurement that is more than the selected number of standard deviations above the mean.

10. The method of claim 9 wherein the selected number of standard deviations is between about 1.0 and about 2.0.

* * * * *